United States Patent
Takumi et al.

(10) Patent No.: US 12,234,487 B2
(45) Date of Patent: Feb. 25, 2025

(54) FLAVIN-CONJUGATED GLUCOSE DEHYDROGENASE

(71) Applicant: IKEDA FOOD RESEARCH CO., LTD., Hiroshima (JP)

(72) Inventors: Takafumi Takumi, Hiroshima (JP); Emi Watanabe, Hiroshima (JP); Ryo Takenaka, Hiroshima (JP); Hirokazu Sanada, Hiroshima (JP); Michinari Honda, Hiroshima (JP)

(73) Assignee: IKEDA FOOD RESEARCH CO., LTD., Hiroshima (JP)

( * ) Notice: Subject to any disclaimer, the term of this patent is extended or adjusted under 35 U.S.C. 154(b) by 1063 days.

(21) Appl. No.: 17/049,119

(22) PCT Filed: Apr. 15, 2019

(86) PCT No.: PCT/JP2019/016161
§ 371 (c)(1),
(2) Date: Oct. 20, 2020

(87) PCT Pub. No.: WO2019/208308
PCT Pub. Date: Oct. 31, 2019

(65) Prior Publication Data
US 2021/0238562 A1  Aug. 5, 2021

(30) Foreign Application Priority Data
Apr. 23, 2018 (JP) .................. 2018-093351

(51) Int. Cl.
C12N 9/00 (2006.01)
C12N 9/04 (2006.01)
G01N 33/535 (2006.01)

(52) U.S. Cl.
CPC ......... *C12N 9/0006* (2013.01); *G01N 33/535* (2013.01); *C12Y 101/05* (2013.01); *G01N 2333/902* (2013.01)

(58) Field of Classification Search
CPC ...... C12N 9/0006; C12N 9/0004; C12Q 1/32; C12Q 1/006; C12Y 101/9901; C12Y 101/05; G01N 33/66; G01N 2333/904; G01N 27/327

USPC ........................................... 435/190
See application file for complete search history.

(56) References Cited

U.S. PATENT DOCUMENTS

| | | | |
|---|---|---|---|
| 7,514,250 B2 | 4/2009 | Omura et al. |
| 8,445,246 B2 | 5/2013 | Tajima et al. |
| 8,492,130 B2 | 7/2013 | Yada et al. |
| 8,691,547 B2 | 4/2014 | Omura et al. |
| 9,487,758 B2 | 11/2016 | Sumida et al. |
| 2014/0154777 A1 | 6/2014 | Sumida et al. |

FOREIGN PATENT DOCUMENTS

| | | |
|---|---|---|
| JP | 2015-139376 | 8/2015 |
| WO | 2004/058958 | 7/2004 |
| WO | 2006/101239 | 9/2006 |
| WO | 2008/001903 | 1/2008 |
| WO | 2010/140431 | 12/2010 |
| WO | 2013/022074 | 2/2013 |

OTHER PUBLICATIONS

International Search Report (ISR) issued Jul. 2, 2019 in International (PCT) Application No. PCT/JP2019/016161.

*Primary Examiner* — Robert B Mondesi
*Assistant Examiner* — Mohammad Y Meah
(74) *Attorney, Agent, or Firm* — Wenderoth, Lind & Ponack, L.L.P.

(57) ABSTRACT

The present invention addresses the problem of providing: a glucose dehydrogenase; a polynucleotide encoding the enzyme; a method for producing the enzyme; a method for measuring glucose using the enzyme; a measurement reagent composition; and a biosensor. The present invention pertains to a protein that has any of amino acid sequences (a), (b) and (c) and has a glucose dehydrogenase activity, etc.: (a) an amino acid sequence represented by SEQ ID NO: 3, 6, 15 or 16; (b) an amino acid sequence derived from the amino acid sequence represented by SEQ ID NO: 3, 6, 15 or 16 by deleting, substituting or adding 1-3 amino acids; and (c) an amino acid sequence having 90% or more identity to the amino acid sequence represented by SEQ ID NO: 3 or 15 or 85% or more identity to the amino acid sequence represented by SEQ ID NO: 6 or 16.

5 Claims, 1 Drawing Sheet
Specification includes a Sequence Listing.

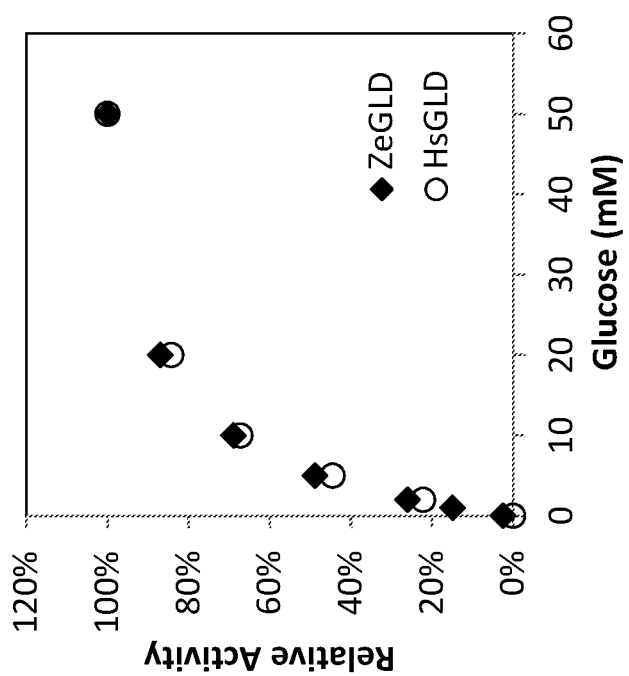

SEQUENCE LISTING

```
<160> NUMBER OF SEQ ID NOS: 16

<210> SEQ ID NO 1
<211> LENGTH: 2086
<212> TYPE: DNA
<213> ORGANISM: Zygorhynchus exponens

<400> SEQUENCE: 1
atgaaaatct ctgctgctat tggaactatt attgtagcat ttgcttccta tgctacagct      60
caatcacaag gtactactag taccgatact tttgactatg ttatcgttgg tggtggtgta     120
ggaggtaaag taaacaatgt atacgcgata aaaccttgct ctaacacttg tttacttta     180 aggtttggcc ttggcaagtc gtctttctga taataaagat gttacagttg ctgtcctcga     240
agcaggtccc aatgcagatg atcgatttgt tgtttatgct ccctgcatgt aagtgtaaat     300
tttctcttgt aaaacatttg ctaatctatt gataattagg tatggtcagg ctgtaggtac     360
```

```
tgaactttgt cctcttgtcc ctactactcc ccaagagaac atgggtaaca gaagccttac    420
catcgctact ggtaaattac ttggcggtgg tagtgctgtc aatggtctcg tctgggtaag    480
gctatattac atgttaattt ataaaagcaa gagcttgaag ttaatttacc atgatttatt    540
ttagactcgt ggtgcattga agactttga cgcttgggaa gagcttggta atcctggatg     600
gaacggcgcc agtatgttcc aatactttaa aaaggtagag aaatttactc cacccactcc    660
cgctcaagaa gaatatggtg ctactgctca aaagaatgtt catggtactt ctggtcgtat    720
tcaagtttct ttcacaaact tgaattcccc ccaatctgcc agctggaatg catctctcca    780
ttcacttgac tttactgctg tccctgatct cttgaatggt acacttcacg gttattccac    840
aactcctaat actttagacc ctgcaactgc ccgtcgtgta gatgcttacg ccggctacat    900
tgccccctac gttagccgtc ataaccttgc cgtcttggcc aaccataccg tttctcgtat    960
tcagtttgct cctagaaaag gaatgagcc tcttcgcgcc actggtgttg aatggtatcc    1020
tactggtgac aagtctcaca agcaagtatt gaaggctcgt cgtgaagtca tcgtttcttc    1080
tggttctatt ggtagtccca agcttttgga agtctctggg attggtaaca aggatattgt    1140
cactgctgct ggtgttaaat cattaattga cttgcctggt gttggttcca acatgcaaga    1200
tcacgtacat gccgttactg tttctaccac aaacatcgcg ggttacacta ccaacagtat    1260
cttcaccaac gatactcttg ctgcggaaga aagacaaaag tatgttaaca acaagactgg    1320
catttacact actacaccca acaatcttgg ttatccttcc cctagccaac tcttcaaggg    1380
tacctctttt gtttctggta agaatttgc tgcaagaatt cgtcaatctg ctgatacctg    1440
ggctaaacat tatgctgcta ccaattcatc cactgctgag ttgatcaaga acaatacgc    1500 tatcattgct agtcgttatg aagaaaacta catgtctccc atcgaaatca acttgactcc    1560
tggctacggt ggaactgcta atgttgacct cgccaaaaac aagtatcaaa ctgttaacca    1620
cgtcttgatt gctcctcttt ctcgtggtca tactcatatt aaatccgctg atattgaggc    1680
ccccgctgaa gtaaatcctc aatactactc taacccctatg gatttggatg tccatgttgc   1740
ctctactaag cttgcccgta gaattattac tgcttctccc ggtcttggtg accttaacag    1800
tggtgaggtt gaacctggaa ctcatgtcac cagcgacgat gatgttcgca cctggttgtc    1860
caacaacgtt cgttccgact ggcatcctgt tggtacttgt gctatgcttc ccaaggaatt    1920
gggtggtgtc gttgatccca atctcaaggt ttatggtaca gccaacttgc gtgtcgttga    1980
cgcctctgtt atgcctcttg aagtctcttc tcacttgatg caacccactt atggtgtcgc    2040
tgaaaaggct gctgatatca tcaagtctac ttacaaaaag cactaa                   2086
```

<210> SEQ ID NO 2
<211> LENGTH: 1917
<212> TYPE: DNA
<213> ORGANISM: Zygorhynchus exponens
<220> FEATURE:
<221> NAME/KEY: CDS
<222> LOCATION: (1)..(1917)

<400> SEQUENCE: 2

```
atg aag atc tct gct gct atc gtc act gtt gtt aca gca ttt act tcg    48
Met Lys Ile Ser Ala Ala Ile Val Thr Val Val Thr Ala Phe Thr Ser
1               5                   10                  15 ttt gct acg gct cag caa caa aac acc agt agc acc gat atc tac gac    96
Phe Ala Thr Ala Gln Gln Gln Asn Thr Ser Ser Thr Asp Ile Tyr Asp
            20                  25                  30 tat gtt atc gtt ggt ggt ggt gta gga ggt ttg gcc ttg gct agt cgt   144
Tyr Val Ile Val Gly Gly Gly Val Gly Gly Leu Ala Leu Ala Ser Arg
```

```
                        35                  40                  45
ctt tct gaa aac aag aat gtc act gtt gct gtc ctc gag gca ggt cct      192
Leu Ser Glu Asn Lys Asn Val Thr Val Ala Val Leu Glu Ala Gly Pro
 50                  55                  60 tat gca ggc gac cag ttt gtt gtt tat gct ccc ggc atg tat ggc caa      240
Tyr Ala Gly Asp Gln Phe Val Val Tyr Ala Pro Gly Met Tyr Gly Gln
 65                  70                  75                  80 gct gta ggt act gac ctt tgt cct ctt gtt cct act tct ccc caa gag      288
Ala Val Gly Thr Asp Leu Cys Pro Leu Val Pro Thr Ser Pro Gln Glu
                 85                  90                  95 aac atg ggt aac aga agc ctt acc att gct act ggt aaa ttg ctt ggc      336
Asn Met Gly Asn Arg Ser Leu Thr Ile Ala Thr Gly Lys Leu Leu Gly
            100                 105                 110 ggc ggt agt gct gtc aat ggc ctt gtc tgg acc cgt ggc gca ttg aaa      384
Gly Gly Ser Ala Val Asn Gly Leu Val Trp Thr Arg Gly Ala Leu Lys
        115                 120                 125 gat ttt gac gct tgg gaa gaa ctc ggt aat cct ggc tgg aac ggc aac      432
Asp Phe Asp Ala Trp Glu Glu Leu Gly Asn Pro Gly Trp Asn Gly Asn
130                 135                 140 aac ctg ttc aag tac ttt aat aag gtt gaa aac ttt act cct ccc act      480
Asn Leu Phe Lys Tyr Phe Asn Lys Val Glu Asn Phe Thr Pro Pro Thr
145                 150                 155                 160 cca gct caa gca aca tat ggt gct act tac caa aag aac gcc cac ggt      528
Pro Ala Gln Ala Thr Tyr Gly Ala Thr Tyr Gln Lys Asn Ala His Gly
                165                 170                 175 acg aag gga cct atc gat atc tcg ttt aca aat ttt gaa ttc cct caa      576
Thr Lys Gly Pro Ile Asp Ile Ser Phe Thr Asn Phe Glu Phe Pro Gln
            180                 185                 190 tct gcc aac tgg aat gca tct ctc gat aca ctt gac ttt act gct gtc      624
Ser Ala Asn Trp Asn Ala Ser Leu Asp Thr Leu Asp Phe Thr Ala Val
        195                 200                 205 ccc gat ctc ttg aac ggt acg ctt cac ggt tac tcc acg aca ccc aac      672
Pro Asp Leu Leu Asn Gly Thr Leu His Gly Tyr Ser Thr Thr Pro Asn
210                 215                 220 act ctg gac cct gcg act gct cgt cgt gcc gac gct tac gct ggt tac      720
Thr Leu Asp Pro Ala Thr Ala Arg Arg Ala Asp Ala Tyr Ala Gly Tyr
225                 230                 235                 240 atc gag ccc tac aca agc cgt aat aac ctc gct gtc ttg gcc aac tat      768
Ile Glu Pro Tyr Thr Ser Arg Asn Asn Leu Ala Val Leu Ala Asn Tyr
                245                 250                 255 act gtt tct cgt atc cag ttt gct cct aga cag ggc aag caa cct ctt      816
Thr Val Ser Arg Ile Gln Phe Ala Pro Arg Gln Gly Lys Gln Pro Leu
            260                 265                 270 cgc gcc acc ggt gtt gag tgg tat ccg act ggt gac aaa tct aaa aag      864
Arg Ala Thr Gly Val Glu Trp Tyr Pro Thr Gly Asp Lys Ser Lys Lys
        275                 280                 285 caa gtc ttg aag gct cgt tac gaa gtc atc ctc tct tct ggt gct att      912
Gln Val Leu Lys Ala Arg Tyr Glu Val Ile Leu Ser Ser Gly Ala Ile
290                 295                 300 ggc agt cct aag ctt ttg gaa ctt tct ggc gtt gga aac aag aat att      960
Gly Ser Pro Lys Leu Leu Glu Leu Ser Gly Val Gly Asn Lys Asn Ile
305                 310                 315                 320 gtc act gct gct ggt gtt caa tca ttg att gat tta cct ggt gtt ggt     1008
Val Thr Ala Ala Gly Val Gln Ser Leu Ile Asp Leu Pro Gly Val Gly
                325                 330                 335 tcc aat ctg caa gat cac gta cat gcc gtt act gtc tct acc aca aac     1056
Ser Asn Leu Gln Asp His Val His Ala Val Thr Val Ser Thr Thr Asn
            340                 345                 350 atc ccc ggt tat act acc aac agc atc ttc acc aac gat act ctc gct     1104
```

```
                Ile Pro Gly Tyr Thr Thr Asn Ser Ile Phe Thr Asn Asp Thr Leu Ala
                                355                 360                 365 gaa gag caa aga cag ctg tat gct gat aac aag acc ggt att tac aca     1152
Glu Glu Gln Arg Gln Leu Tyr Ala Asp Asn Lys Thr Gly Ile Tyr Thr
        370                 375                 380 acc aca ccc aac aac ctc ggc tac cct tct ccc agc caa ctc ttc aat     1200
Thr Thr Pro Asn Asn Leu Gly Tyr Pro Ser Pro Ser Gln Leu Phe Asn
385                 390                 395                 400 ggt act tca ttc gtt tct ggt aaa gaa ttt gcc gca aaa att cgt aac     1248
Gly Thr Ser Phe Val Ser Gly Lys Glu Phe Ala Ala Lys Ile Arg Asn
                405                 410                 415 acc act gac att tgg gct gaa cgt tat gct gcc aac aat gct tcc aat     1296
Thr Thr Asp Ile Trp Ala Glu Arg Tyr Ala Ala Asn Asn Ala Ser Asn
        420                 425                 430 gct gaa ttg ctc aag aga caa tat gct atc gtt gct agt cgc tat gaa     1344
Ala Glu Leu Leu Lys Arg Gln Tyr Ala Ile Val Ala Ser Arg Tyr Glu
435                 440                 445 gaa aac tac ttg tct cct atc gaa atc aac ttg act ccc ggc tat ggt     1392
Glu Asn Tyr Leu Ser Pro Ile Glu Ile Asn Leu Thr Pro Gly Tyr Gly
                450                 455                 460 ggt act gct aaa gtt aac ctc acc agc aat aaa tat caa act gtc aac     1440
Gly Thr Ala Lys Val Asn Leu Thr Ser Asn Lys Tyr Gln Thr Val Asn
465                 470                 475                 480 cac gtc ttg att gct cct ctc tct cgt ggt tat acc cat att aaa tca     1488
His Val Leu Ile Ala Pro Leu Ser Arg Gly Tyr Thr His Ile Lys Ser
                485                 490                 495 gct gat att gaa gac ccc gta gat atc aat cct caa tac tac tct cat     1536
Ala Asp Ile Glu Asp Pro Val Asp Ile Asn Pro Gln Tyr Tyr Ser His
        500                 505                 510 ccc ttg gat ttg gat gtc cat gtt gct tct act aag ctt gct cgt caa     1584
Pro Leu Asp Leu Asp Val His Val Ala Ser Thr Lys Leu Ala Arg Gln
        515                 520                 525 atc att act gct tct ccc ggt ctt ggc gat atc aac agt ggc gag act     1632
Ile Ile Thr Ala Ser Pro Gly Leu Gly Asp Ile Asn Ser Gly Glu Thr
530                 535                 540 gaa cca ggt atg aat gtc acc agt gat gaa gat gtt cgt aag tgg ctg     1680
Glu Pro Gly Met Asn Val Thr Ser Asp Glu Asp Val Arg Lys Trp Leu
545                 550                 555                 560 gcc gac aat gtt cgt tca gat tgg cat cct gtt ggt act tgc gct atg     1728
Ala Asp Asn Val Arg Ser Asp Trp His Pro Val Gly Thr Cys Ala Met
                565                 570                 575 att ccc aag gaa ttg ggt ggc gtg gtt gat ccc agt ctc aag gtt tat     1776
Ile Pro Lys Glu Leu Gly Gly Val Val Asp Pro Ser Leu Lys Val Tyr
        580                 585                 590 ggt aca gcg aac ttg cgt gta gtc gat gct tct gtt atg cct ctt gaa     1824
Gly Thr Ala Asn Leu Arg Val Val Asp Ala Ser Val Met Pro Leu Glu
        595                 600                 605 gtg tct tct cac ttg atg ctc ccc act tat ggt gtt gct gag aag gct     1872
Val Ser Ser His Leu Met Leu Pro Thr Tyr Gly Val Ala Glu Lys Ala
610                 615                 620 gct gat atc atc aag tct gtt tac aag aag caa aat aat ctt tag         1917
Ala Asp Ile Ile Lys Ser Val Tyr Lys Lys Gln Asn Asn Leu
625                 630                 635

<210> SEQ ID NO 3
<211> LENGTH: 638
<212> TYPE: PRT
<213> ORGANISM: Zygorhynchus exponens

<400> SEQUENCE: 3
```

```
Met Lys Ile Ser Ala Ile Val Thr Val Thr Ala Phe Thr Ser
1               5                   10                  15

Phe Ala Thr Ala Gln Gln Asn Thr Ser Thr Asp Ile Tyr Asp
            20                  25                  30

Tyr Val Ile Val Gly Gly Val Gly Gly Leu Ala Leu Ala Ser Arg
            35              40                  45

Leu Ser Glu Asn Lys Asn Val Thr Val Ala Val Leu Glu Ala Gly Pro
50                  55                      60

Tyr Ala Gly Asp Gln Phe Val Val Tyr Ala Pro Gly Met Tyr Gly Gln
65                      70                  75                  80

Ala Val Gly Thr Asp Leu Cys Pro Leu Val Pro Thr Ser Pro Gln Glu
                85                  90                  95

Asn Met Gly Asn Arg Ser Leu Thr Ile Ala Thr Gly Lys Leu Leu Gly
            100                 105                 110

Gly Gly Ser Ala Val Asn Gly Leu Val Trp Thr Arg Gly Ala Leu Lys
            115                 120                 125

Asp Phe Asp Ala Trp Glu Glu Leu Gly Asn Pro Gly Trp Asn Gly Asn
        130                 135                 140

Asn Leu Phe Lys Tyr Phe Asn Lys Val Glu Asn Phe Thr Pro Pro Thr
145                 150                 155                 160

Pro Ala Gln Ala Thr Tyr Gly Ala Thr Tyr Gln Lys Asn Ala His Gly
                    165                 170                 175

Thr Lys Gly Pro Ile Asp Ile Ser Phe Thr Asn Phe Glu Phe Pro Gln
                180                 185                 190

Ser Ala Asn Trp Asn Ala Ser Leu Asp Thr Leu Asp Phe Thr Ala Val
            195                 200                 205

Pro Asp Leu Leu Asn Gly Thr Leu His Gly Tyr Ser Thr Thr Pro Asn
        210                 215                 220

Thr Leu Asp Pro Ala Thr Ala Arg Arg Ala Asp Ala Tyr Ala Gly Tyr
225                 230                 235                 240

Ile Glu Pro Tyr Thr Ser Arg Asn Asn Leu Ala Val Leu Ala Asn Tyr
                    245                 250                 255

Thr Val Ser Arg Ile Gln Phe Ala Pro Arg Gln Gly Lys Gln Pro Leu
            260                 265                 270

Arg Ala Thr Gly Val Glu Trp Tyr Pro Thr Gly Asp Lys Ser Lys Lys
            275                 280                 285

Gln Val Leu Lys Ala Arg Tyr Glu Val Ile Leu Ser Ser Gly Ala Ile
        290                 295                 300

Gly Ser Pro Lys Leu Leu Glu Leu Ser Gly Val Gly Asn Lys Asn Ile
305                 310                 315                 320

Val Thr Ala Ala Gly Val Gln Ser Leu Ile Asp Leu Pro Gly Val Gly
                325                 330                 335

Ser Asn Leu Gln Asp His Val His Ala Val Thr Val Ser Thr Thr Asn
            340                 345                 350

Ile Pro Gly Tyr Thr Thr Asn Ser Ile Phe Thr Asn Asp Thr Leu Ala
        355                 360                 365

Glu Glu Gln Arg Gln Leu Tyr Ala Asp Asn Lys Thr Gly Ile Tyr Thr
370                 375                 380

Thr Thr Pro Asn Asn Leu Gly Tyr Pro Ser Pro Ser Gln Leu Phe Asn
385                 390                 395                 400

Gly Thr Ser Phe Val Ser Gly Lys Glu Phe Ala Ala Lys Ile Arg Asn
                    405                 410                 415

Thr Thr Asp Ile Trp Ala Glu Arg Tyr Ala Ala Asn Asn Ala Ser Asn
```

```
                        420             425             430
Ala Glu Leu Leu Lys Arg Gln Tyr Ala Ile Val Ala Ser Arg Tyr Glu
            435                 440                 445

Glu Asn Tyr Leu Ser Pro Ile Glu Ile Asn Leu Thr Pro Gly Tyr Gly
            450                 455                 460

Gly Thr Ala Lys Val Asn Leu Thr Ser Asn Lys Tyr Gln Thr Val Asn
465                 470                 475                 480

His Val Leu Ile Ala Pro Leu Ser Arg Gly Tyr Thr His Ile Lys Ser
            485                 490                 495

Ala Asp Ile Glu Asp Pro Val Asp Ile Asn Pro Gln Tyr Tyr Ser His
            500                 505                 510

Pro Leu Asp Leu Asp Val His Val Ala Ser Thr Lys Leu Ala Arg Gln
            515                 520                 525

Ile Ile Thr Ala Ser Pro Gly Leu Gly Asp Ile Asn Ser Gly Glu Thr
            530                 535                 540

Glu Pro Gly Met Asn Val Thr Ser Asp Glu Asp Val Arg Lys Trp Leu
545                 550                 555                 560

Ala Asp Asn Val Arg Ser Asp Trp His Pro Val Gly Thr Cys Ala Met
            565                 570                 575

Ile Pro Lys Glu Leu Gly Gly Val Val Asp Pro Ser Leu Lys Val Tyr
            580                 585                 590

Gly Thr Ala Asn Leu Arg Val Val Asp Ala Ser Val Met Pro Leu Glu
            595                 600                 605

Val Ser Ser His Leu Met Leu Pro Thr Tyr Gly Val Ala Glu Lys Ala
            610                 615                 620

Ala Asp Ile Ile Lys Ser Val Tyr Lys Lys Gln Asn Asn Leu
625                 630                 635

<210> SEQ ID NO 4
<211> LENGTH: 2086
<212> TYPE: DNA
<213> ORGANISM: Hyphomucor sp.

<400> SEQUENCE: 4
atgaaaatct ctgctgctat tggaactatt attgtagcat ttgcttccta tgctacagct      60
caatcacaag gtactactag taccgatact tttgactatg ttatcgttgg tggtggtgta     120
ggaggtaaag taaacaatgt atacgcgata aaaccttgct ctaacacttg tttacttta      180 aggtttggcc ttggcaagtc gtctttctga taataaagat gttacagttg ctgtcctcga     240
agcaggtccc aatgcagatg atcgatttgt tgtttatgct ccctgcatgt aagtgtaaat     300
tttctcttgt aaaacatttg ctaatctatt gataattagg tatggtcagg ctgtaggtac     360
tgaactttgt cctcttgtcc ctactactcc ccaagagaac atgggtaaca gaagccttac     420
catcgctact ggtaaattac ttggcggtgg tagtgctgtc aatggtctcg tctgggtaag     480
gctatattac atgttaattt ataaaagcaa gagcttgaag ttaatttacc atgatttatt     540
ttagactcgt ggtgcattga agactttga cgcttgggaa gagcttggta atcctggatg      600
gaacggcgcc agtatgttcc aatactttaa aaaggtagag aaatttactc cacccactcc     660
cgctcaagaa gaatatggtg ctactgctca aaagaatgtt catggtactt ctggtcgtat     720 tcaagttct ttcacaaact tgaattccc ccaatctgcc agctggaatg catctctcca      780
ttcacttgac tttactgctg tccctgatct cttgaatggt acacttcacg gttattccac     840
aactcctaat actttagacc ctgcaactgc ccgtcgtgta gatgcttacg ccggctacat     900
```

| | |
|---|---|
| tgcccctac gttagccgtc ataaccttgc cgtcttggcc aaccataccg tttctcgtat | 960 |
| tcagtttgct cctagaaaag gaaatgagcc tcttcgcgcc actggtgttg aatggtatcc | 1020 |
| tactggtgac aagtctcaca agcaagtatt gaaggctcgt cgtgaagtca tcgtttcttc | 1080 |
| tggttctatt ggtagtccca agcttttgga agtctctggt attggtaaca aggatattgt | 1140 |
| cactgctgct ggtgttaaat cattaattga cttgcctggt gttggttcca acatgcaaga | 1200 |
| tcacgtacat gccgttactg tttctaccac aaacatcgct ggttacacta ccaacagtat | 1260 |
| cttcaccaac gatactcttg ctgcggaaga aagacaaaag tatgttaaca acaagactgg | 1320 |
| catttacact actacaccca acaatcttgg ttatccttcc cctagccaac tcttcaaggg | 1380 |
| tacctctttt gtttctggta aagaatttgc tgcaagaatt cgtcaatctg ctgataccctg | 1440 |
| ggctaaacat tatgctgcta ccaattcatc cactgctgag ttgatcaaga acaatacgc | 1500 |
| tatcattgct agtcgttatg aagaaaacta catgtctccc atcgaaatca acttgactcc | 1560 |
| tggctacgtt ggaactgcta atgttgacct cgccaaaaac aagtatcaaa ctgttaacca | 1620 |
| cgtcttgatt gctcctcttt ctcgtggtca tactcatatt aaatccgctg atattgaggc | 1680 |
| cccgctgaa gtaaatcctc aatactactc taacccatg gatttggatg tccatgttgc | 1740 |
| ctctactaag cttgcccgta gaattattac tgcttctccc ggtcttggtg accttaacag | 1800 |
| tggtgaggtt gaacctggaa ctcatgtcac cagcgacgat gatgttcgca cctggttgtc | 1860 |
| caacaacgtt cgttccgact ggcatcctgt tggtacttgt gctatgcttc ccaaggaatt | 1920 |
| gggtggtgtc gttgatccca atctcaaggt ttatggtaca gccaacttgc gtgtcgttga | 1980 |
| cgcctctgtt atgcctcttg aagtctcttc tcacttgatg caacccactt atggtgtcgc | 2040 |
| tgaaaaggct gctgatatca tcaagtctac ttacaaaaag cactaa | 2086 |

```
<210> SEQ ID NO 5
<211> LENGTH: 1908
<212> TYPE: DNA
<213> ORGANISM: Hyphomucor sp.
<220> FEATURE:
<221> NAME/KEY: CDS
<222> LOCATION: (1)..(1908)

<400> SEQUENCE: 5
```

| | | |
|---|---|---|
| atg aaa atc tct gct gct att gga act att att gta gca ttt gct tcc<br>Met Lys Ile Ser Ala Ala Ile Gly Thr Ile Ile Val Ala Phe Ala Ser<br>1               5                   10                  15 | | 48 |
| tat gct aca gct caa tca caa ggt act act agt acc gat act ttt gac<br>Tyr Ala Thr Ala Gln Ser Gln Gly Thr Thr Ser Thr Asp Thr Phe Asp<br>            20                  25                  30 | | 96 |
| tat gtt atc gtt ggt ggt ggt gta gga ggt ttg gcc ttg gca agt cgt<br>Tyr Val Ile Val Gly Gly Gly Val Gly Gly Leu Ala Leu Ala Ser Arg<br>        35                  40                  45 | | 144 |
| ctt tct gat aat aaa gat gtt aca gtt gct gtc ctc gaa gca ggt ccc<br>Leu Ser Asp Asn Lys Asp Val Thr Val Ala Val Leu Glu Ala Gly Pro<br>    50                  55                  60 | | 192 |
| aat gca gat gat cga ttt gtt gtt tat gct ccc tgc atg tat ggt cag<br>Asn Ala Asp Asp Arg Phe Val Val Tyr Ala Pro Cys Met Tyr Gly Gln<br>65                  70                  75                  80 | | 240 |
| gct gta ggt act gaa ctt tgt cct ctt gtc cct act act ccc caa gag<br>Ala Val Gly Thr Glu Leu Cys Pro Leu Val Pro Thr Thr Pro Gln Glu<br>                85                  90                  95 | | 288 |
| aac atg ggt aac aga agc ctt acc atc gct act ggt aaa tta ctt ggc<br>Asn Met Gly Asn Arg Ser Leu Thr Ile Ala Thr Gly Lys Leu Leu Gly<br>            100                 105                 110 | | 336 |

```
ggt ggt agt gct gtc aat ggt ctc gtc tgg act cgt ggt gca ttg aaa        384
Gly Gly Ser Ala Val Asn Gly Leu Val Trp Thr Arg Gly Ala Leu Lys
        115                 120                 125 gac ttt gac gct tgg gaa gag ctt ggt aat cct gga tgg aac ggc gcc        432
Asp Phe Asp Ala Trp Glu Glu Leu Gly Asn Pro Gly Trp Asn Gly Ala
130                 135                 140 agt atg ttc caa tac ttt aaa aag gta gag aaa ttt act cca ccc act        480
Ser Met Phe Gln Tyr Phe Lys Lys Val Glu Lys Phe Thr Pro Pro Thr
145                 150                 155                 160 ccc gct caa gaa gaa tat ggt gct act gct caa aag aat gtt cat ggt        528
Pro Ala Gln Glu Glu Tyr Gly Ala Thr Ala Gln Lys Asn Val His Gly
                165                 170                 175 act tct ggt cgt att caa gtt tct ttc aca aac ttt gaa ttc ccc caa        576
Thr Ser Gly Arg Ile Gln Val Ser Phe Thr Asn Phe Glu Phe Pro Gln
            180                 185                 190 tct gcc agc tgg aat gca tct ctc cat tca ctt gac ttt act gct gtc        624
Ser Ala Ser Trp Asn Ala Ser Leu His Ser Leu Asp Phe Thr Ala Val
        195                 200                 205 cct gat ctc ttg aat ggt aca ctt cac ggt tat tcc aca act cct aat        672
Pro Asp Leu Leu Asn Gly Thr Leu His Gly Tyr Ser Thr Thr Pro Asn
210                 215                 220 act tta gac cct gca act gcc cgt cgt gta gat gct tac gcc ggc tac        720
Thr Leu Asp Pro Ala Thr Ala Arg Arg Val Asp Ala Tyr Ala Gly Tyr
225                 230                 235                 240 att gcc ccc tac gtt agc cgt cat aac ctt gcc gtc ttg gcc aac cat        768
Ile Ala Pro Tyr Val Ser Arg His Asn Leu Ala Val Leu Ala Asn His
                245                 250                 255 acc gtt tct cgt att cag ttt gct cct aga aaa gga aat gag cct ctt        816
Thr Val Ser Arg Ile Gln Phe Ala Pro Arg Lys Gly Asn Glu Pro Leu
            260                 265                 270 cgc gcc act ggt gtt gaa tgg tat cct act ggt gac aag tct cac aag        864
Arg Ala Thr Gly Val Glu Trp Tyr Pro Thr Gly Asp Lys Ser His Lys
        275                 280                 285 caa gta ttg aag gct cgt cgt gaa gtc atc gtt tct tct ggt tct att        912
Gln Val Leu Lys Ala Arg Arg Glu Val Ile Val Ser Ser Gly Ser Ile
290                 295                 300 ggt agt ccc aag ctt ttg gaa gtc tct ggt att ggt aac aag gat att        960
Gly Ser Pro Lys Leu Leu Glu Val Ser Gly Ile Gly Asn Lys Asp Ile
305                 310                 315                 320 gtc act gct gct ggt gtt aaa tca tta att gac ttg cct ggt gtt ggt       1008
Val Thr Ala Ala Gly Val Lys Ser Leu Ile Asp Leu Pro Gly Val Gly
                325                 330                 335 tcc aac atg caa gat cac gta cat gcc gtt act gtt tct acc aca aac       1056
Ser Asn Met Gln Asp His Val His Ala Val Thr Val Ser Thr Thr Asn
            340                 345                 350 atc gct ggt tac act acc aac agt atc ttc acc aac gat act ctt gct       1104
Ile Ala Gly Tyr Thr Thr Asn Ser Ile Phe Thr Asn Asp Thr Leu Ala
        355                 360                 365 gcg gaa gaa aga caa aag tat gtt aac aac aag act ggc att tac act       1152
Ala Glu Glu Arg Gln Lys Tyr Val Asn Asn Lys Thr Gly Ile Tyr Thr
370                 375                 380 act aca ccc aac aat ctt ggt tat cct tcc cct agc caa ctc ttc aag       1200
Thr Thr Pro Asn Asn Leu Gly Tyr Pro Ser Pro Ser Gln Leu Phe Lys
385                 390                 395                 400 ggt acc tct ttt gtt tct ggt aaa gaa ttt gct gca aga att cgt caa       1248
Gly Thr Ser Phe Val Ser Gly Lys Glu Phe Ala Ala Arg Ile Arg Gln
                405                 410                 415 tct gct gat acc tgg gct aaa cat tat gct gct acc aat tca tcc act       1296
Ser Ala Asp Thr Trp Ala Lys His Tyr Ala Ala Thr Asn Ser Ser Thr
            420                 425                 430
```

```
gct gag ttg atc aag aaa caa tac gct atc att gct agt cgt tat gaa    1344
Ala Glu Leu Ile Lys Lys Gln Tyr Ala Ile Ile Ala Ser Arg Tyr Glu
            435                 440                 445 gaa aac tac atg tct ccc atc gaa atc aac ttg act cct ggc tac ggt    1392
Glu Asn Tyr Met Ser Pro Ile Glu Ile Asn Leu Thr Pro Gly Tyr Gly
    450                 455                 460 gga act gct aat gtt gac ctc gcc aaa aac aag tat caa act gtt aac    1440
Gly Thr Ala Asn Val Asp Leu Ala Lys Asn Lys Tyr Gln Thr Val Asn
465                 470                 475                 480 cac gtc ttg att gct cct ctt tct cgt ggt cat act cat att aaa tcc    1488
His Val Leu Ile Ala Pro Leu Ser Arg Gly His Thr His Ile Lys Ser
                485                 490                 495 gct gat att gag gcc ccc gct gaa gta aat cct caa tac tac tct aac    1536
Ala Asp Ile Glu Ala Pro Ala Glu Val Asn Pro Gln Tyr Tyr Ser Asn
        500                 505                 510 cct atg gat ttg gat gtc cat gtt gcc tct act aag ctt gcc cgt aga    1584
Pro Met Asp Leu Asp Val His Val Ala Ser Thr Lys Leu Ala Arg Arg
            515                 520                 525 att att act gct tct ccc ggt ctt ggt gac ctt aac agt ggt gag gtt    1632
Ile Ile Thr Ala Ser Pro Gly Leu Gly Asp Leu Asn Ser Gly Glu Val
530                 535                 540 gaa cct gga act cat gtc acc agc gac gat gat gtt cgc acc tgg ttg    1680
Glu Pro Gly Thr His Val Thr Ser Asp Asp Asp Val Arg Thr Trp Leu
545                 550                 555                 560 tcc aac aac gtt cgt tcc gac tgg cat cct gtt ggt act tgt gct atg    1728
Ser Asn Asn Val Arg Ser Asp Trp His Pro Val Gly Thr Cys Ala Met
                565                 570                 575 ctt ccc aag gaa ttg ggt ggt gtc gtt gat ccc aat ctc aag gtt tat    1776
Leu Pro Lys Glu Leu Gly Gly Val Val Asp Pro Asn Leu Lys Val Tyr
        580                 585                 590 ggt aca gcc aac ttg cgt gtc gtt gac gcc tct gtt atg cct ctt gaa    1824
Gly Thr Ala Asn Leu Arg Val Val Asp Ala Ser Val Met Pro Leu Glu
            595                 600                 605 gtc tct tct cac ttg atg caa ccc act tat ggt gtc gct gaa aag gct    1872
Val Ser Ser His Leu Met Gln Pro Thr Tyr Gly Val Ala Glu Lys Ala
610                 615                 620 gct gat atc atc aag tct act tac aaa aag cac taa                    1908
Ala Asp Ile Ile Lys Ser Thr Tyr Lys Lys His
625                 630                 635

<210> SEQ ID NO 6
<211> LENGTH: 635
<212> TYPE: PRT
<213> ORGANISM: Hyphomucor sp.

<400> SEQUENCE: 6

Met Lys Ile Ser Ala Ala Ile Gly Thr Ile Val Ala Phe Ala Ser
1               5                   10                  15

Tyr Ala Thr Ala Gln Ser Gln Gly Thr Thr Ser Thr Asp Thr Phe Asp
                20                  25                  30

Tyr Val Ile Val Gly Gly Gly Val Gly Gly Leu Ala Leu Ala Ser Arg
            35                  40                  45

Leu Ser Asp Asn Lys Asp Val Thr Val Ala Val Leu Glu Ala Gly Pro
        50                  55                  60

Asn Ala Asp Asp Arg Phe Val Val Tyr Ala Pro Cys Met Tyr Gly Gln
65                  70                  75                  80

Ala Val Gly Thr Glu Leu Cys Pro Leu Val Pro Thr Thr Pro Gln Glu
                85                  90                  95
```

```
Asn Met Gly Asn Arg Ser Leu Thr Ile Ala Thr Gly Lys Leu Leu Gly
                100                 105                 110

Gly Gly Ser Ala Val Asn Gly Leu Val Trp Thr Arg Gly Ala Leu Lys
        115                 120                 125

Asp Phe Asp Ala Trp Glu Glu Leu Gly Asn Pro Gly Trp Asn Gly Ala
    130                 135                 140

Ser Met Phe Gln Tyr Phe Lys Lys Val Glu Lys Phe Thr Pro Pro Thr
145                 150                 155                 160

Pro Ala Gln Glu Glu Tyr Gly Ala Thr Ala Gln Lys Asn Val His Gly
                165                 170                 175

Thr Ser Gly Arg Ile Gln Val Ser Phe Thr Asn Phe Glu Phe Pro Gln
            180                 185                 190

Ser Ala Ser Trp Asn Ala Ser Leu His Ser Leu Asp Phe Thr Ala Val
        195                 200                 205

Pro Asp Leu Leu Asn Gly Thr Leu His Gly Tyr Ser Thr Thr Pro Asn
    210                 215                 220

Thr Leu Asp Pro Ala Thr Ala Arg Arg Val Asp Ala Tyr Ala Gly Tyr
225                 230                 235                 240

Ile Ala Pro Tyr Val Ser Arg His Asn Leu Ala Val Leu Ala Asn His
                245                 250                 255

Thr Val Ser Arg Ile Gln Phe Ala Pro Arg Lys Gly Asn Glu Pro Leu
            260                 265                 270

Arg Ala Thr Gly Val Glu Trp Tyr Pro Thr Gly Asp Lys Ser His Lys
        275                 280                 285

Gln Val Leu Lys Ala Arg Arg Glu Val Ile Val Ser Ser Gly Ser Ile
    290                 295                 300

Gly Ser Pro Lys Leu Leu Glu Val Ser Gly Ile Gly Asn Lys Asp Ile
305                 310                 315                 320

Val Thr Ala Ala Gly Val Lys Ser Leu Ile Asp Leu Pro Gly Val Gly
                325                 330                 335

Ser Asn Met Gln Asp His Val His Ala Val Thr Val Ser Thr Thr Asn
            340                 345                 350

Ile Ala Gly Tyr Thr Thr Asn Ser Ile Phe Thr Asn Asp Thr Leu Ala
        355                 360                 365

Ala Glu Glu Arg Gln Lys Tyr Val Asn Asn Lys Thr Gly Ile Tyr Thr
    370                 375                 380

Thr Thr Pro Asn Asn Leu Gly Tyr Pro Ser Pro Ser Gln Leu Phe Lys
385                 390                 395                 400

Gly Thr Ser Phe Val Ser Gly Lys Glu Phe Ala Ala Arg Ile Arg Gln
                405                 410                 415

Ser Ala Asp Thr Trp Ala Lys His Tyr Ala Ala Thr Asn Ser Ser Thr
            420                 425                 430

Ala Glu Leu Ile Lys Lys Gln Tyr Ala Ile Ile Ala Ser Arg Tyr Glu
        435                 440                 445

Glu Asn Tyr Met Ser Pro Ile Glu Ile Asn Leu Thr Pro Gly Tyr Gly
    450                 455                 460

Gly Thr Ala Asn Val Asp Leu Ala Lys Asn Lys Tyr Gln Thr Val Asn
465                 470                 475                 480

His Val Leu Ile Ala Pro Leu Ser Arg Gly Thr His Ile Lys Ser
                485                 490                 495

Ala Asp Ile Glu Ala Pro Ala Glu Val Asn Pro Gln Tyr Tyr Ser Asn
            500                 505                 510

Pro Met Asp Leu Asp Val His Val Ala Ser Thr Lys Leu Ala Arg Arg
```

515                 520                 525
Ile Ile Thr Ala Ser Pro Gly Leu Gly Asp Leu Asn Ser Gly Glu Val
                530                 535                 540

Glu Pro Gly Thr His Val Thr Ser Asp Asp Val Arg Thr Trp Leu
545                 550                 555                 560

Ser Asn Asn Val Arg Ser Asp Trp His Pro Val Gly Thr Cys Ala Met
                    565                 570                 575

Leu Pro Lys Glu Leu Gly Gly Val Val Asp Pro Asn Leu Lys Val Tyr
                580                 585                 590

Gly Thr Ala Asn Leu Arg Val Val Asp Ala Ser Val Met Pro Leu Glu
                595                 600                 605

Val Ser Ser His Leu Met Gln Pro Thr Tyr Gly Val Ala Glu Lys Ala
                610                 615                 620

Ala Asp Ile Ile Lys Ser Thr Tyr Lys Lys His
625                 630                 635

<210> SEQ ID NO 7
<211> LENGTH: 37
<212> TYPE: DNA
<213> ORGANISM: Artificial Sequence
<220> FEATURE:
<223> OTHER INFORMATION: primer:F6309-Ori

<400> SEQUENCE: 7
ccgcagctcg tcaaaatgaa gatctctgct gctatcg                              37

<210> SEQ ID NO 8
<211> LENGTH: 26
<212> TYPE: DNA
<213> ORGANISM: Artificial Sequence
<220> FEATURE:
<223> OTHER INFORMATION: primer:F6309-R-1st

<400> SEQUENCE: 8
gttcatttaa agattatttt gcttct                                          26

<210> SEQ ID NO 9
<211> LENGTH: 44
<212> TYPE: DNA
<213> ORGANISM: Artificial Sequence
<220> FEATURE:
<223> OTHER INFORMATION: primer:F6309-R-2nd

<400> SEQUENCE: 9
gttacgcttc tagagcatgc gttcatttaa agattatttt gctt                      44

<210> SEQ ID NO 10
<211> LENGTH: 37
<212> TYPE: DNA
<213> ORGANISM: Artificial Sequence
<220> FEATURE:
<223> OTHER INFORMATION: primer:F6292-Ori

<400> SEQUENCE: 10
ccgcagctcg tcaaaatgaa aatctctgct gctattg                              37

<210> SEQ ID NO 11
<211> LENGTH: 28
<212> TYPE: DNA
<213> ORGANISM: Artificial Sequence
<220> FEATURE:
<223> OTHER INFORMATION: primer:F6292-R-1st

```
<400> SEQUENCE: 11
gttcatttag tgcttttttgt aagtagac                                        28

<210> SEQ ID NO 12
<211> LENGTH: 39
<212> TYPE: DNA
<213> ORGANISM: Artificial Sequence
<220> FEATURE:
<223> OTHER INFORMATION: primer:F6292-R-2nd

<400> SEQUENCE: 12
gttacgcttc tagagcatgc gttcatttag tgcttttttg                            39

<210> SEQ ID NO 13
<211> LENGTH: 35
<212> TYPE: DNA
<213> ORGANISM: Artificial Sequence
<220> FEATURE:
<223> OTHER INFORMATION: primer:F6292-PP-F

<400> SEQUENCE: 13
gctgaagctg aattccaatc acaaggtact actag                                 35

<210> SEQ ID NO 14
<211> LENGTH: 36
<212> TYPE: DNA
<213> ORGANISM: Artificial Sequence
<220> FEATURE:
<223> OTHER INFORMATION: primer:F6292-PP-R

<400> SEQUENCE: 14 gagttttttgt tctagattag tgcttttttgt aagtag                              36

<210> SEQ ID NO 15
<211> LENGTH: 618
<212> TYPE: PRT
<213> ORGANISM: Zygorhynchus exponens

<400> SEQUENCE: 15
```

Gln Gln Gln Asn Thr Ser Ser Thr Asp Ile Tyr Asp Tyr Val Ile Val
1               5                   10                  15

Gly Gly Gly Val Gly Gly Leu Ala Leu Ala Ser Arg Leu Ser Glu Asn
            20                  25                  30

Lys Asn Val Thr Val Ala Val Leu Glu Ala Gly Pro Tyr Ala Gly Asp
        35                  40                  45

Gln Phe Val Val Tyr Ala Pro Gly Met Tyr Gly Gln Ala Val Gly Thr
    50                  55                  60

Asp Leu Cys Pro Leu Val Pro Thr Ser Pro Gln Glu Asn Met Gly Asn
65                  70                  75                  80

Arg Ser Leu Thr Ile Ala Thr Gly Lys Leu Leu Gly Gly Gly Ser Ala
                85                  90                  95

Val Asn Gly Leu Val Trp Thr Arg Gly Ala Leu Lys Asp Phe Asp Ala
            100                 105                 110

Trp Glu Glu Leu Gly Asn Pro Gly Trp Asn Gly Asn Asn Leu Phe Lys
        115                 120                 125

Tyr Phe Asn Lys Val Glu Asn Phe Thr Pro Thr Pro Ala Gln Ala
    130                 135                 140

Thr Tyr Gly Ala Thr Tyr Gln Lys Asn Ala His Gly Thr Lys Gly Pro
145                 150                 155                 160

Ile Asp Ile Ser Phe Thr Asn Phe Glu Phe Pro Gln Ser Ala Asn Trp

```
                165                 170                 175
Asn Ala Ser Leu Asp Thr Leu Asp Phe Thr Ala Val Pro Asp Leu Leu
            180                 185                 190

Asn Gly Thr Leu His Gly Tyr Ser Thr Thr Pro Asn Thr Leu Asp Pro
        195                 200                 205

Ala Thr Ala Arg Arg Ala Asp Ala Tyr Ala Gly Tyr Ile Glu Pro Tyr
    210                 215                 220

Thr Ser Arg Asn Asn Leu Ala Val Leu Ala Asn Tyr Thr Val Ser Arg
225                 230                 235                 240

Ile Gln Phe Ala Pro Arg Gln Gly Lys Gln Pro Leu Arg Ala Thr Gly
                245                 250                 255

Val Glu Trp Tyr Pro Thr Gly Asp Lys Ser Lys Gln Val Leu Lys
            260                 265                 270

Ala Arg Tyr Glu Val Ile Leu Ser Ser Gly Ala Ile Gly Ser Pro Lys
        275                 280                 285

Leu Leu Glu Leu Ser Gly Val Gly Asn Lys Asn Ile Val Thr Ala Ala
    290                 295                 300

Gly Val Gln Ser Leu Ile Asp Leu Pro Gly Val Gly Ser Asn Leu Gln
305                 310                 315                 320

Asp His Val His Ala Val Thr Val Ser Thr Thr Asn Ile Pro Gly Tyr
                325                 330                 335

Thr Thr Asn Ser Ile Phe Thr Asn Asp Thr Leu Ala Glu Glu Gln Arg
            340                 345                 350

Gln Leu Tyr Ala Asp Asn Lys Thr Gly Ile Tyr Thr Thr Thr Pro Asn
        355                 360                 365

Asn Leu Gly Tyr Pro Ser Pro Ser Gln Leu Phe Asn Gly Thr Ser Phe
    370                 375                 380

Val Ser Gly Lys Glu Phe Ala Ala Lys Ile Arg Asn Thr Asp Ile
385                 390                 395                 400

Trp Ala Glu Arg Tyr Ala Ala Asn Asn Ala Ser Asn Ala Glu Leu Leu
                405                 410                 415

Lys Arg Gln Tyr Ala Ile Val Ala Ser Arg Tyr Glu Glu Asn Tyr Leu
            420                 425                 430

Ser Pro Ile Glu Ile Asn Leu Thr Pro Gly Tyr Gly Gly Thr Ala Lys
        435                 440                 445

Val Asn Leu Thr Ser Asn Lys Tyr Gln Thr Val Asn His Val Leu Ile
    450                 455                 460

Ala Pro Leu Ser Arg Gly Tyr Thr His Ile Lys Ser Ala Asp Ile Glu
465                 470                 475                 480

Asp Pro Val Asp Ile Asn Pro Gln Tyr Tyr Ser His Pro Leu Asp Leu
                485                 490                 495

Asp Val His Val Ala Ser Thr Lys Leu Ala Arg Gln Ile Ile Thr Ala
            500                 505                 510

Ser Pro Gly Leu Gly Asp Ile Asn Ser Gly Glu Thr Glu Pro Gly Met
        515                 520                 525

Asn Val Thr Ser Asp Glu Asp Val Arg Lys Trp Leu Ala Asp Asn Val
    530                 535                 540

Arg Ser Asp Trp His Pro Val Gly Thr Cys Ala Met Ile Pro Lys Glu
545                 550                 555                 560

Leu Gly Gly Val Val Asp Pro Ser Leu Lys Val Tyr Gly Thr Ala Asn
                565                 570                 575

Leu Arg Val Val Asp Ala Ser Val Met Pro Leu Glu Val Ser Ser His
            580                 585                 590
```

```
Leu Met Leu Pro Thr Tyr Gly Val Ala Glu Lys Ala Ala Asp Ile Ile
            595                 600                 605

Lys Ser Val Tyr Lys Lys Gln Asn Asn Leu
        610                 615

<210> SEQ ID NO 16
<211> LENGTH: 615
<212> TYPE: PRT
<213> ORGANISM: Hyphomucor sp.

<400> SEQUENCE: 16

Gln Ser Gln Gly Thr Thr Ser Thr Asp Thr Phe Asp Tyr Val Ile Val
1               5                   10                  15

Gly Gly Gly Val Gly Gly Leu Ala Leu Ala Ser Arg Leu Ser Asp Asn
            20                  25                  30

Lys Asp Val Thr Val Ala Val Leu Glu Ala Gly Pro Asn Ala Asp Asp
        35                  40                  45

Arg Phe Val Val Tyr Ala Pro Cys Met Tyr Gly Gln Ala Val Gly Thr
    50                  55                  60

Glu Leu Cys Pro Leu Val Pro Thr Thr Pro Gln Glu Asn Met Gly Asn
65                  70                  75                  80

Arg Ser Leu Thr Ile Ala Thr Gly Lys Leu Leu Gly Gly Gly Ser Ala
                85                  90                  95

Val Asn Gly Leu Val Trp Thr Arg Gly Ala Leu Lys Asp Phe Asp Ala
            100                 105                 110

Trp Glu Glu Leu Gly Asn Pro Gly Trp Asn Gly Ala Ser Met Phe Gln
        115                 120                 125

Tyr Phe Lys Lys Val Glu Lys Phe Thr Pro Pro Thr Pro Ala Gln Glu
    130                 135                 140

Glu Tyr Gly Ala Thr Ala Gln Lys Asn Val His Gly Thr Ser Gly Arg
145                 150                 155                 160

Ile Gln Val Ser Phe Thr Asn Phe Glu Phe Pro Gln Ser Ala Ser Trp
                165                 170                 175

Asn Ala Ser Leu His Ser Leu Asp Phe Thr Ala Val Pro Asp Leu Leu
            180                 185                 190

Asn Gly Thr Leu His Gly Tyr Ser Thr Thr Pro Asn Thr Leu Asp Pro
        195                 200                 205

Ala Thr Ala Arg Arg Val Asp Ala Tyr Ala Gly Tyr Ile Ala Pro Tyr
    210                 215                 220

Val Ser Arg His Asn Leu Ala Val Leu Ala Asn His Thr Val Ser Arg
225                 230                 235                 240

Ile Gln Phe Ala Pro Arg Lys Gly Asn Glu Pro Leu Arg Ala Thr Gly
                245                 250                 255

Val Glu Trp Tyr Pro Thr Gly Asp Lys Ser His Lys Gln Val Leu Lys
            260                 265                 270

Ala Arg Arg Glu Val Ile Val Ser Ser Gly Ser Ile Gly Ser Pro Lys
        275                 280                 285

Leu Leu Glu Val Ser Gly Ile Gly Asn Lys Asp Ile Val Thr Ala Ala
    290                 295                 300

Gly Val Lys Ser Leu Ile Asp Leu Pro Gly Val Gly Ser Asn Met Gln
305                 310                 315                 320

Asp His Val His Ala Val Thr Val Ser Thr Thr Asn Ile Ala Gly Tyr
                325                 330                 335

Thr Thr Asn Ser Ile Phe Thr Asn Asp Thr Leu Ala Ala Glu Glu Arg
```

```
              340                 345                 350
Gln Lys Tyr Val Asn Asn Lys Thr Gly Ile Tyr Thr Thr Thr Pro Asn
        355                 360                 365

Asn Leu Gly Tyr Pro Ser Pro Ser Gln Leu Phe Lys Gly Thr Ser Phe
        370                 375                 380

Val Ser Gly Lys Glu Phe Ala Ala Arg Ile Arg Gln Ser Ala Asp Thr
385                 390                 395                 400

Trp Ala Lys His Tyr Ala Ala Thr Asn Ser Ser Thr Ala Glu Leu Ile
                405                 410                 415

Lys Lys Gln Tyr Ala Ile Ile Ala Ser Arg Tyr Glu Glu Asn Tyr Met
                420                 425                 430

Ser Pro Ile Glu Ile Asn Leu Thr Pro Gly Tyr Gly Gly Thr Ala Asn
        435                 440                 445

Val Asp Leu Ala Lys Asn Lys Tyr Gln Thr Val Asn His Val Leu Ile
        450                 455                 460

Ala Pro Leu Ser Arg Gly His Thr His Ile Lys Ser Ala Asp Ile Glu
465                 470                 475                 480

Ala Pro Ala Glu Val Asn Pro Gln Tyr Tyr Ser Asn Pro Met Asp Leu
                485                 490                 495

Asp Val His Val Ala Ser Thr Lys Leu Ala Arg Arg Ile Ile Thr Ala
                500                 505                 510

Ser Pro Gly Leu Gly Asp Leu Asn Ser Gly Glu Val Glu Pro Gly Thr
        515                 520                 525

His Val Thr Ser Asp Asp Val Arg Thr Trp Leu Ser Asn Asn Val
530                 535                 540

Arg Ser Asp Trp His Pro Val Gly Thr Cys Ala Met Leu Pro Lys Glu
545                 550                 555                 560

Leu Gly Gly Val Val Asp Pro Asn Leu Lys Val Tyr Gly Thr Ala Asn
                565                 570                 575

Leu Arg Val Val Asp Ala Ser Val Met Pro Leu Glu Val Ser Ser His
                580                 585                 590

Leu Met Gln Pro Thr Tyr Gly Val Ala Glu Lys Ala Ala Asp Ile Ile
        595                 600                 605

Lys Ser Thr Tyr Lys Lys His
610                 615
```

FLAVIN-CONJUGATED GLUCOSE DEHYDROGENASE

TECHNICAL FIELD

The present invention relates to a glucose dehydrogenase, a polynucleotide encoding the enzyme, a method for manufacturing the enzyme, a method for measuring glucose using the enzyme, a measuring reagent composition, a biosensor and the like.

BACKGROUND ART

Measurement of a blood glucose (blood sugar) concentration is important primarily in blood sugar control for a diabetes patient. For measuring blood sugar, biosensors are widely used as blood sugar meters utilizing enzymes.

As enzymes usable for biosensors, glucose oxidases and glucose dehydrogenases are known. However, the glucose oxidases had problems that measurement errors are caused by dissolved oxygen in the blood. Among the glucose dehydrogenases, flavin-conjugated glucose dehydrogenases derived from eukaryotic cells are not affected by dissolved oxygen, require no addition of coenzymes, and have an excellent substrate specificity, and thus they are useful as enzymes for biosensors (Patent Documents 1 to 5).

PRIOR ART DOCUMENTS

Patent Documents

Patent Document 1: International Publication No. WO 2004/058958
Patent Document 2: International Publication No. WO 2006/101239
Patent Document 3: International Publication No. WO 2008/001903
Patent Document 4: International Publication No. WO 2010/140431
Patent Document 5: International Publication No. WO 2013/022074

SUMMARY OF INVENTION

Problem to be Solved

The present invention provides a novel glucose dehydrogenase with high substrate specificity, a polynucleotide encoding the enzyme, a method for manufacturing the enzyme, a method for measuring glucose using the enzyme, a measuring reagent composition and a biosensor. Furthermore, the present invention provides methods for manufacturing the measuring reagent composition and the biosensor.

Solution to Problem

The inventors searched for various microorganism-derived glucose dehydrogenases, and then found a flavin-conjugated (flavin-binding) glucose dehydrogenase with high substrate specificity. Furthermore, the inventors found an efficient method for manufacturing the flavin-conjugated glucose dehydrogenase to complete the present invention.

That is, the present invention relates to the following aspects [1] to [9].
[1] A protein having the following amino acid sequence (a), (b) or (c), and having glucose dehydrogenase activity:
 (a) an amino acid sequence represented by SEQ ID NO: 3, 6, 15 or 16;
 (b) an amino acid sequence in which 1 to 3 amino acids are deleted from, replaced in or added to the amino acid sequence represented by SEQ ID NO: 3, 6, 15 or 16;
 (c) an amino acid sequence which has at least 90% identity with the amino acid sequence represented by SEQ ID NO: 3 or 15, or alternatively, an amino acid sequence which has at least 85% identity with the amino acid sequence represented by SEQ ID NO: 6 or 16.
[2] A polynucleotide encoding the protein according to [1].
[3] A recombinant vector containing the polynucleotide according to [2].
[4] A transformant cell containing the polynucleotide according to [2].
[5] A method for manufacturing a flavin-conjugated glucose dehydrogenase, characterized in that the cell according to [4] is cultured, and the flavin-conjugated glucose dehydrogenase is collected from the culture.
[6] A flavin-conjugated glucose dehydrogenase obtained by the manufacturing method according to [5].
[7] A method for measuring glucose using the flavin-conjugated glucose dehydrogenase according to [1] or [6].
[8] A reagent composition for measuring glucose, containing the flavin-conjugated glucose dehydrogenase according to [1] or [6].
[9] A biosensor for measuring glucose, containing the flavin-conjugated glucose dehydrogenase according to [1] or [6].

Effects of the Invention

The present invention provides a novel flavin-conjugated glucose dehydrogenase with high substrate specificity so as to facilitate the manufacture of the enzyme. Furthermore, the present invention allows to measure glucose using the enzyme so that a glucose measuring reagent composition and a biosensor for measuring glucose can be manufactured.

BRIEF DESCRIPTION OF DRAWINGS

FIG. 1 illustrates a FIGURE showing results from measurements of D-glucose by an enzyme of the present invention.

DESCRIPTION OF EMBODIMENTS

The glucose dehydrogenase according to the present invention is a protein having the following amino acid sequence (a), (b) or (c) and glucose dehydrogenase activity. The "protein" includes a glycoprotein.
 (a) An amino acid sequence represented by SEQ ID NO: 3, 6, 15 or 16.
 (b) An amino acid sequence in which from 1 to 3 amino acids are deleted from, replaced in, or added to the amino acid sequence represented by SEQ ID NO: 3, 6, 15 or 16.
 (c) An amino acid sequence which has at least 90% identity with the amino acid sequence represented by SEQ ID NO: 3 or 15, or at least 85% identity with the amino acid sequence represented by SEQ ID NO: 6 or 16.

The enzyme is a protein preferably composed of the amino acid sequence (a), (b) or (c) and having glucose dehydrogenase activity.

The glucose dehydrogenase of the present invention is not particularly limited as long as it is a protein having the above-described sequence, and it may be an enzyme obtained by culturing cells or a synthetic enzyme obtained by synthesis. Preferably, it is a recombinant enzyme obtained by gene recombination.

The flavin-conjugated glucose dehydrogenase of the present invention has the following properties (1) to (4). The flavin may include a flavin adenine dinucleotide (FAD) and a flavin mononucleotide (FMN), and the FAD is preferable.

(1) action: the enzyme catalyzes a reaction in which glucose is oxidized in the presence of an electron acceptor.
(2) soluble.
(3) oxygen is not substantially used as an electron acceptor.
(4) The substrate specificity is high. When activity on 50 mM of glucose is taken to be 100%, activity on 50 mM of maltose is preferably at most 2.0%, more preferably at most 1.5%, even more preferably at most 1.0%.

The polynucleotide according to the present invention is composed of following (i), (ii), (iii) or (iv) and encodes proteins having glucose dehydrogenase activity:

(i) A polynucleotide encoding the amino acid sequence according to the above-mentioned (a), (b) or (c).
(ii) A polynucleotide having a base sequence represented by SEQ ID NO: 1, 2, 4 or 5.
(iii) A polynucleotide in which 3, 6 or 9 bases are deleted from or added to the base sequence represented by SEQ ID NO: 1, 2, 4 or 5. Alternatively, a polynucleotide having a base sequence in which 1 to 10, preferably 9, 8, 6, 5, 4, 3 or 2 bases are replaced in the base sequence represented by SEQ ID NO: 1, 2, 4 or 5.
(iv) A polynucleotide encoding a protein which has a base sequence having identity with the base sequence represented by SEQ ID NO: 1, 2, 4 or 5.

The identity is preferably at least 90%, 92% or 95%, more preferably at least 97%, 98% or 99%.

The term "identity" used herein means a value of identity calculated by BLAST analysis of NCBI.

The recombinant vector of the present invention is a cloning vector or an expression vector, and the vector can be appropriately selected. The vector contains the polynucleotide of the present invention as an insert. The polynucleotide as the insert may be a polynucleotide for which the codon usage is optimized according to a host cell. An expression level of the recombinant protein may be improved by replacing a stop codon by a stop codon optimal for the host. In addition, the polynucleotide may be a polynucleotide encoding an amino acid sequence including a signal sequence or not including a signal sequence as long as it can be expressed in a host. For example, when the polynucleotide is a polynucleotide encoding an amino acid sequence such as SEQ ID NOs; 15 and 16 not including a signal sequence, the polynucleotide can be inserted into the vector with a start codon ATG being added, or it can be inserted as it is so as to utilize a peptide for expression or the signal sequence on the vector side. Alternatively, the polynucleotide may be a polynucleotide in which a sequence encoding a signal sequence is replaced by a sequence encoding a signal sequence appropriate for a host, for example. Note that, as required, a polynucleotide encoding expression-contributing proteins such as a chaperon and a lysozyme can be introduced into the same vector as that of the polynucleotide of the present invention, and/or can be introduced into another vector so as to be held in the same host. Furthermore, the glucose dehydrogenase of the present invention can also be expressed by using a vector which can express it as a fusion protein to which various tags such as His tag, FLAG tag and GFP are added.

When the recombinant protein is expressed in the prokaryotic cell, a cDNA sequence not including intron can be used as the insert, and the expression vector can be exemplified by a pUC system, pBluescriptII, a pET expression system, a pGEX expression system, a pCold expression system, etc.

When the recombinant protein is expressed in the eukaryotic cell, the polynucleotide as the insert may be a DNA sequence including intron such as SEQ ID NOs: 1 and 4, or a cDNA sequence such as SEQ ID NOs: 2 and 5. The expression vector can be exemplified by pGAPZα, pKA1, pCDM8, pSVK3, pSVL, pBK-CMV, pBK-RSV, EBV vector, pRS, pYE82, etc.

For example, prokaryotic cells such as *Escherichia coli* and *Bacillus subtilis*, eukaryotic cells such as Eumycetes (yeast, filamentous fungus (ascomycete, basidiomycete, etc.), insect cell and mammal cell, etc. can be used as the host cell, and the transformant cell of the present invention can be obtained by introducing the vector of the present invention into that cell in order to transform it. The vector may be preserved in the transformant cell in a state like a plasmid or may be preserved with being incorporated into a chromosome. Alternatively, the transformant cell containing the polynucleotide of the present invention can be obtained by using a gene editing technique. Furthermore, although the host can be appropriately selected according to necessities of sugar chains and other peptide modifications, preferably a host capable of adding a sugar chain is selected to produce an enzyme having a sugar chain (glycoprotein).

A glucose dehydrogenase can be collected from a culture obtained by culturing the transformant cell of the present invention to manufacture a recombinant glucose dehydrogenase.

For culturing microorganisms used in the present invention, conventional medium for culturing microorganisms can be used. Either a synthesized medium or a natural medium may be used, as long as the medium moderately contains carbon sources, nitrogen sources, minerals and other micronutrients required by the microorganisms of use. As the carbon sources, glucose, sucrose, dextrin, starch, glycerol, molasses, etc. can be used. As the nitrogen sources, inorganic salts such as ammonium chloride, ammonium nitrate, ammonium sulfate and ammonium phosphate, amino acids such as DL-alanine and L-glutamic acid, nitrogen-containing natural products such as peptone, meat extract, yeast extract, malt extract and corn steep liquor can be used. As the minerals, monosodium phosphate, disodium phosphate, monopotassium phosphate, dipotassium phosphate, magnesium sulfate, ferric chloride, etc. can be used.

The culturing for obtaining the glucose dehydrogenase of the present invention should be generally carried out under an aerobic condition by a method such as shake culture and aeration agitation. A culture condition suitable for production of the glucose dehydrogenase should be set in consideration of the properties of a glucose dehydrogenase-producing bacterium. For example, the culturing is carried out preferably at a culture temperature of 20° C. to 50° C., in a range of pH 4 to pH 8, and the pH may be adjusted during the culture in consideration of producibility. The culture period is preferably 2 to 10 days. By culturing with such a method, the glucose dehydrogenase can be produced and accumulated in a culture.

For the method for obtaining the glucose dehydrogenase from a culture, a conventional method for manufacturing proteins can be used. For example, first, a glucose dehydrogenase-producing bacterium is cultured, and then a culture supernatant is obtained by centrifugation. Alternatively, the cultured fungus body is obtained, the cultured microorganism is crushed by an appropriate manner, and supernatants are obtained from the crushed liquid by centrifugation or the like. Next, the glucose dehydrogenase contained in these supernatants can be purified by a conventional method for purifying proteins to obtain a purified enzyme. For example, the glucose dehydrogenase can be purified by combining purifying manipulations such as ultrafiltration, salt precipitation, solvent precipitation, heat treatment, dialysis, ion-exchange chromatography, hydrophobic chromatography, gel filtration and affinity chromatography.

The glucose dehydrogenase of the present invention can be used in a dried state. Although the drying method is not limited as long as the enzyme is not deactivated, it is preferable to obtain a lyophilized product through lyophilization. In the drying process, a buffer solution agent and a stabilizer can be added. It may be crushed and powderized so as to obtain a powdered product.

Glucose can be measured by using the glucose dehydrogenase of the present invention. The method for measuring glucose of the present invention can include a step for bringing the test sample containing glucose into contact with the glucose dehydrogenase of the present invention, so as to quantify glucose in a test sample. Although the test sample in the present invention is not particularly limited, it can be exemplified by biological samples, specifically blood, tear, saliva, urine or interstitial fluid, etc. The enzyme of the present invention is useful particularly for measuring blood sugar.

The present invention provides a manufacturing method for manufacturing a reagent composition for measuring glucose, a kit for measuring glucose, or a biosensor for measuring glucose using the glucose dehydrogenase of the present invention. Since the enzyme of the present has high substrate specificity and does not use oxygen as an electron acceptor, it is hardly affected by other saccharides and dissolved oxygen in the measured sample. Therefore, the reagent composition for measuring glucose, the kit for measuring glucose or the biosensor for measuring glucose which are hardly affected by other saccharides and dissolved oxygen can be provided, allowing the glucose measurement with high measurement accuracy.

The reagent composition for measuring glucose of the present invention may be any reagent composition as long as it contains the glucose dehydrogenase of the present invention as an enzyme. The amount of the enzyme in the composition is not particularly limited as long as the glucose in samples can be measured, but the amount of the enzyme per measurement is preferably about 0.01 to 100 U, more preferably about 0.05 to 50 U, and further preferably about 0.1 to 20 U. The composition preferably contains a buffer, and any other optional components known to those skilled in the art such as a stabilizer are preferably contained to enhance thermal stability and storage stability of the enzyme and reagent components. The above components can be exemplified by a bovine serum albumin (BSA) or egg albumin, a sugar or a sugar alcohol not interactive with the enzyme, a carboxyl group-containing compound, an alkaline earth metal compound, an ammonium salt, sulfate, proteins or the like. Furthermore, a known substance which reduces the influence from impurities affecting the measurement in the test sample may also be contained in the measuring reagent. The kit for measuring glucose of the present invention contains the above-mentioned reagent composition and can contain a glucose standard solution.

The biosensor of the present invention may be any sensor as long as it contains the glucose dehydrogenase of the present invention as an enzyme. For example, a sensor containing in its reaction layer the glucose dehydrogenase of the present invention as an enzyme, such as an electrochemical biosensor, is made by comprising a substrate, a counter electrode, a working electrode, a mediator and the above-described enzyme. The mediator can be exemplified by a proteinic electronic mediator such as heme, a ferricyanide compound, a quinone compound, an osmium compound, a phenazine compound, a phenothiazine compound, etc. Moreover, a biosensor adapted to detecting ion change, coloring intensity, pH change or the like can also be constituted. Glucose measurement is possible by using this biosensor.

Furthermore, the glucose dehydrogenase of the present invention can be used for a bio-battery. The bio-battery of the present invention is composed of an anode electrode for oxidation reaction and a cathode electrode for reduction reaction, and optionally includes an electrolyte layer which separates between the anode and the cathode as required. As an enzyme electrode containing the electron mediators and the glucose dehydrogenase is used for the anode electrode, electrons generated by oxidation of the substrate are collected on the electrode, and protons are generated. Meanwhile, an enzyme to be generally used for the cathode electrode may be used on the cathode side, for example laccase, ascorbate oxidase or bilirubin oxidase is used, and the proton generated on the anode side is reacted with oxygen to generate water. As the electrode, electrodes generally used for the bio-battery, such as carbon, gold and platinum group metal can be used.

In measuring the activity of the enzyme of the present invention, the enzyme is optionally diluted to a final concentration of preferably 0.15-0.6 U/mL for use. Note that a unit of enzyme activity of the enzyme (U) means an enzyme activity for oxidizing 1 μmol of glucose in one minute. The enzyme activity of the glucose dehydrogenase of the present invention can be measured by the following method.

(Method for Measuring Glucose Dehydrogenase (GLD) Activity)

1.00 mL of 100 mM potassium phosphate buffer (pH 6.0), 1.00 mL of 1 M D-glucose solution, 0.14 mL of 3 mM 2,6-dichlorophenolindophenol (hereinafter called DCIP), and 0.20 mL of 3 mM 1-methoxy-5-methylphenazinium methylsulfate, as well as 0.61 mL of ultrapure water were mixed, kept at 37° C. for 10 minutes, and then 0.05 mL of enzyme solution was added, and the reaction was initiated. For 5 minutes from the initiation of the reaction, a decrement per one minute of the absorbance at 600 nm ($\Delta A600$) associated with progression of the enzyme reaction was measured to calculate the enzyme activity from a straight part according to the following formula. In this measurement, for the enzyme activity, an enzyme amount for reducing 1 μmol of DCIP at 37° C., pH 6.0 per one minute was defined as 1U.

Glucose dehydrogenase (GLD) activity (U/mL)=(−($\Delta A600$−$\Delta A600$ blank)×3.0×dilution ratio of enzyme)/(10.8×1.0×0.05)

Note that, in the formula, 3.0 represents a liquid volume (mL) of the reaction reagent+the enzyme solution, 10.8 represents a molar absorption coefficient of DCIP at pH 6.0, 1.0 represents an optical path length (cm) of a cell, 0.05 represents a liquid volume (mL) of the enzyme solution, and $\Delta A600$blank represents a decrement of the absorbance at 600 nm per minute in the case that the reaction is initiated by adding a dilute solution for the enzyme instead of the enzyme solution.

EXAMPLES

Hereinafter, the present invention will be specifically explained by Examples. However, the present invention is not limited by the following Examples.

Example 1

(Cloning of the Flavin-Conjugated Glucose Dehydrogenase (GLD))

GLD-producing bacteria were searched. As a result, GLD activity has been confirmed in the culture supernatants of *Zygorhynchus exponens* Burgeff var. *exponens* NBRC100517 and *Hyphomucor* sp.RD055426. The GLD derived from *Z. exponens* Burgeff var. *exponens* NBRC100517 is referred to as ZeGLD, and the GLD derived from *H.* sp.RD055426 is referred to as HsGLD.

(1) Culture of Fungus Bodies

A liquid medium consisting of 4% (w/v) of Pinedex (Matsutani Chemical Industry Co., Ltd.), 1% (w/v) of defatted soybean (Showa Sangyo Co., Ltd.), 1% (w/v) of corn steep liquor (San-ei Sucrochemical Co., Ltd.), 0.5% (w/v) of potassium dihydrogenphosphate (NACALAI TESQUE, INC.), 0.05% (w/v) of magnesium sulfate heptahydrate (NACALAI TESQUE, INC.) and water was adjusted to have a pH of 6.0, and 10 mL of the liquid medium was introduced into each of two big test tube and autoclaved at 121° C. for 20 minutes. The GLD-producing bacteria were inoculated to the cooled liquid media and shake-cultured at 25° C. for 72 hours, and then each moist fungus body was collected by means of bleached cloth.

(2) Extraction of Genomic DNA

After 200 mg of each of the moist fungus bodies obtained in (1) was frozen at −80° C., 0.5 mL of a buffer consisting of 200 mM of Tris-HCl (pH 8.0), 50 mM of EDTA, 200 mM of NaCl, and 1% of N-lauroyl sarcosine sodium salt was added thereto and the fungus bodies were crushed. After crushing the fungus bodies, the supernatants of the crushed liquid were subjected to phenol/chloroform treatment and ethanol precipitation so as to obtain genomic DNAs.

(3) Obtaining Genomic DNA Encoding GLD

PCR was carried out by using each of the genomic DNAs obtained in (2) as a template and a primer pair for obtaining the GLD gene. As a result, PCR products considered to be internal sequences of the respective GLD genes were confirmed. Note that the primer pair was designed by the present inventors for obtaining various GLD genes. Each of the PCR products was purified and ligated to T-vector pMD20 (TAKARA BIO INC.) by using DNA Ligation Kit (TAKARA BIO INC.).

Each of the obtained plasmid vectors was introduced into *Escherichia coli* JM109 competent cell (TAKARA BIO INC.) so as to transform the cell. Each of the obtained transformants was cultured, and a plasmid vector was extracted from each of the collected fungus bodies by using NucleoSpin Plasmid QuickPure (TAKARA BIO INC.). Base sequences of the inserts in the respective plasmid vectors were determined, and on the basis of the determined base sequences, primers for clarifying upstream and downstream sequences of the GLD genes were designed. The Inverse PCR method was carried out by using these primers to determine a genomic DNA sequence encoding each of the GLDs. The whole-length DNA sequence encoding ZeGLD from a start codon to a stop codon was represented by SEQ ID NO: 1, and the whole-length DNA sequence encoding HsGLD from a start codon to a stop codon was represented by SEQ ID NO: 4.

(4) Isolation of the Total RNA

After 200 mg of each of the moist fungus bodies obtained in (1) was frozen at −80° C., 100 µg of each of the total RNAs was extracted using ISOGENII (NIPPON GENE CO., LTD.).

(5) Preparation of a cDNA Library

The cDNA libraries were prepared from the total RNAs obtained in (4), respectively, by a reverse transcription reaction using a reverse transcriptase and an oligo dT primer with an adaptor sequence. "SMARTer RACE cDNA Amplification kit" (TAKARA BIO INC.) was used as a reaction reagent, and the reaction condition was adopted to a protocol described in an operating manual.

(6) Preparation of Plasmid Vector for Expression Containing GLD Gene (I)

A plasmid vector was prepared using an amylase-based modified promoter derived from *Aspergillus oryzae* described in Known Document 1 (heterologous gene expression system of *Aspergillus*, Toshitaka MINETOKI, Chemistry and Biology, 38, 12, 831-838, 2000). First, the cDNA libraries obtained in (5) were used as templates to obtain PCR products containing the respective GLD genes. In order to obtain the PCR product containing the ZeGLD gene, a primer pair of the following F4570-Ori (SEQ ID NO: 7) and F6309-R-1st (SEQ ID NO: 8) was used. Also, in order to obtain the PCR product containing the HsGLD gene, a primer pair of the following F6292-Ori (SEQ ID NO: 10) and F6292-R-1st (SEQ ID NO: 11) was used. Then, the above-mentioned PCR products were used as templates to prepare a ZeGLD gene and a HsGLD gene for insertion into the vector. In order to prepare the ZeGLD gene, a primer pair of the following F6309-Ori (SEQ ID NO: 7) and F6309-R-2nd (SEQ ID NO: 9) was used, and in order to prepare the HsGLD gene, a primer pair of the following F6292-Ori (SEQ ID NO: 10) and F6292-R-2nd (SEQ ID NO: 12) was used.

Finally, the prepared GLD genes were bound to the downstream of the promoter to make plasmid vectors on which each of the genes could be expressed. Each of the obtained plasmid vectors for expression was introduced into *Escherichia coli* JM109 competent cell to transform the cell. Each of the resulting transformants was cultured, and the plasmid vector was extracted from each of the collected fungus body using NucleoSpin Plasmid QuickPure. The sequences of the inserts in the plasmid vectors were analyzed so that a base sequence containing each of the GLD gene could be confirmed. The cDNA sequence encoding ZeGLD, the amino acid sequence of ZeGLD, the cDNA sequence encoding HsGLD, and the amino acid sequence of HsGLD were represented by SEQ ID NOs: 2, 3, 5 and 6, respectively.

```
F6309-Ori (SEQ ID NO: 7):
5'-(CCGCAGCTCGTCAAA)ATGAAGATCTCTGCTGCTATCG-3'
(in parentheses: transcription-enhancing factor)

F6309-R-1st (SEQ ID NO: 8):
5'-((GTTCATTTA)) AAGATTATTTTGCTTCT-3'
(in double parentheses: pSENS vector sequence)
```

-continued

```
F6309-R-2nd
                                    (SEQ ID NO: 9)
5'-((GTTACGCTTCTAGAGCATGCGTTCATTTA))AAGATTATTT
TGCTT-3'
(in double parentheses: pSENS vector sequence,
underlined: restriction enzyme site (SphI))

F6292-Ori (SEQ ID NO: 10):
5'-(CCGCAGCTCGTCAAA)ATGAAAATCTCTGCTGCTATTG-3'
(in parentheses: transcription-enhancing factor)

F6292-R-1st (SEQ ID NO: 11):
5'-((GTTCATTTA))GTGCTTTTTGTAAGTAGAC-3'
(in double parentheses: pSENS vector sequence)

F6292-R-2nd (SEQ ID NO: 12):
5'-((GTTACGCTTCTAGAGCATGCGTTCATTTA))GTGCTTTTTG-3'
(in double parentheses: pSENS vector sequence,
underlined: restriction enzyme site (SphI))
```

(7) Obtaining Transformant (I)

Using the plasmid vectors extracted in (6), a recombinant mold (*Aspergillus oryzae*) which produces each of GLD was produced according to methods described in Known Document 2 (Biosci. Biotech. Biochem., 61 (8), 1367-1369, 1997) and Known Document 3 (genetic engineering technique for koji-mold for sake, Katsuya GOMI, journal of Brewing Society of Japan, 494-502, 2000). The obtained recombinant strains were refined in Czapek-Dox solid medium so as to obtain a ZeGLD-producing recombinant mold and an HsGLD-producing recombinant mold. An *Aspergillus oryzae* NS4 strain was used as a host. This strain is available as those being sold in lots at National Research Institute of Brewing, which is Incorporated Administrative Agency.

(8) Confirmation of Recombinant Mold-Derived GLD

A liquid medium consisting of 4% (w/v) of Pinedex, 1% (w/v) of defatted soybean, 1% (w/v) of corn steep liquor, 0.5% (w/v) of potassium dihydrogenphosphate, 0.05% (w/v) of magnesium sulfate heptahydrate and water was adjusted to have a pH of 7.0, and 10 mL of the liquid medium was introduced into each of two big test tube (22 mm×200 mm) and autoclaved at 121° C. for 20 minutes. The recombinant molds obtained in (7) were inoculated to the cooled liquid media and shake-cultured at 30° C. for 72 hours. After completing the culture, the supernatants were collected by centrifugation, and GLD activity was measured by the above-mentioned method for measuring GLD activity. As a result, the GLD activity of the present invention could be confirmed on both supernatants.

(9) Preparation of Plasmid Vector for Expression Containing GLD Gene (II)

A signal prediction program SignalP4.1 was used to predict a signal sequence in the HsGLD amino acid sequence of SEQ ID NO; 6. As a result, the 1st to 20th amino acids were predicted to be the signal sequence. Primers (SEQ ID NOs: 13 and 14) were designed to be able to amplify the gene encoding the amino acid sequence in SEQ ID NO: 16 excluding the predicted signal sequence, and PCR was performed by using the cDNA obtained in (5) as a template. The obtained PCR product was introduced into a secretory plasmid vector pGAPZα (ThermoFisher Scientific, Inc.) to obtain a plasmid vector pGAPZα/HsGLD. This plasmid vector was introduced into *Escherichia coli* JM109 strain to transform the strain. A plasmid was extracted from the obtained transformant, and the sequence of the insert in the plasmid vector was analyzed. As a result, a base sequence was confirmed containing the 61st and subsequent DNA sequence (1848 bp) of SEQ ID NO: 4, which was the HsGLD gene.

In addition, the signal prediction program SignalP4.1 was used to predict a signal sequence in the ZeGLD amino acid sequence of SEQ ID NO; 3. As a result, the 1st to 20th amino acids were predicted to be the signal sequence. A sequence excluding the predicted signal sequence was shown in SEQ ID NO: 15.

```
F6292-PP-F (SEQ ID NO: 13):
5'-(GCTGAAGCTGAATTC)CAATCACAAGGTACTACTAG-3'
(in parentheses: pGAPZα vector sequence)

F6292-PP-R (SEQ ID NO: 14):
5'-(GAGTTTTTGTTCTAGA)TTAGTGCTTTTTGTAAGTAG-3'
(in parentheses: pGAPZα vector sequence)
```

(10) Obtaining Transformant (II)

The plasmid vector (pGAPZα/HsGLD) extracted in (9) was introduced into yeast *Pichia pastoris* KM71H to transform it. This introduction was carried out according to the conditions described in a well-known document (pGAPZ A, B, and C, pGAPZα-A, B, and C, Thermo Fisher Scientific, Rev. Date: 28 Jun. 2010, Manual Part No. 25-0174) so as to make HsGLD-producing recombinant yeast.

(11) Confirmation of Recombinant Yeast-Derived GLD

One hundred and fifty milliliters of BMGY medium consisting of 1.0% of yeast extract (Becton, Dickinson and Company), 2.0% of high polypeptone (Nippon Pharmaceutical Co., Ltd.), 100 mM of potassium phosphate buffer (pH 6.0), 1.34% of Yeast Nitrogen Base without Amino Acids (Sigma-Aldrich Co. LLC), 0.00004% of (+)-biotin (Wako Pure Chemical Industries, Ltd.), and 1.0% of glycerol (Nacalai Tesque) was placed in a Sakaguchi flask with a 500 mL capacity and autoclaved at 121° C. for 20 minutes. The recombinant yeast obtained in (10) was inoculated to the cooled liquid medium and shake-cultured at 30° C. and 120 rpm for 72 hours. After completing the culture, the supernatant was collected by centrifugation, and GLD activity was measured by using a plate reader (Molecular Devices, LLC.) according to the above-mentioned method for measuring GLD activity. As a result, the GLD activity could be confirmed.

Example 2

(Obtaining the Flavin-Conjugated Glucose Dehydrogenase (GLD))

(1) ZeGLD

One hundred and fifty milliliters of the liquid medium described in (8) of Example 1 was introduced into a Sakaguchi flask with a 500 mL capacity and autoclaved at 121° C. for 20 minutes. The ZeGLD-producing recombinant mold obtained in (7) of Example 1 was inoculated to the cooled liquid medium, and shake-cultured at 30° C. for 72 hours to obtain a seed culture liquid. Three-point-five liters of a medium, which was prepared by adding 0.005% (w/v) of chloramphenicol (NACALAI TESQUE, INC.) and an anti-foaming agent to the same composition of the above-mentioned medium, was introduced into a jar fermenter with a 5 L capacity and autoclaved at 121° C. for 30 minutes. One hundred milliliters of the seed culture liquid was inoculated to the cooled liquid medium and cultured at 30° C., 400 rpm, 1 v/v/m for 96 hours. After completing the culture, broth was filtered with a filter cloth, the collected filtrate was centrifuged to collect the supernatant, and furthermore filtrated with a membrane filter (10 µm, Advantech Co., Ltd.) to collect a crude enzyme liquid.

The collected crude enzyme liquid was purified by removing foreign proteins using Cellufine A-500 (JNC CORPORATION) column and TOYOPEARL Butyl-650C (TOSOH CORPORATION) column. The purified sample was concentrated with an ultrafiltration membrane of 8,000 cutoff molecular weight, then water substitution was performed, and the obtained sample was taken to be a ZeGLD sample. When the ZeGLD sample was subjected to a SDS-polyacrylamide electrophoresis method, it was confirmed that ZeGLD exhibited a main band.

(2) HsGLD

The low-molecular-weight components were removed from the culture supernatant cultured by the method described in (11) of Example 1 by using an ultrafiltration membrane of 10,000 cutoff molecular weight (Sartorius AG), and simultaneously the supernatant was concentrated to be an HsGLD sample.

Example 3

(Study of the Enzymatic Properties of GLD of the Present Invention)

Various properties of ZeGLD and HsGLD obtained in Example 2 were evaluated.

(1) Measurement of Absorption Spectrum

The ZeGLD and HsGLD were measured for the absorption spectrum at 300-600 nm before and after addition of D-glucose using a plate reader (Spectra Max Plus 384, Molecular Devices, LLC.). As a result, the absorption maximum shown around 360-380 nm and 450-460 nm disappeared by addition of D-glucose, thus the GLD of the present invention was proved to be a flavin-conjugated protein.

(2) Measurement of Glucose Oxidase (GOD) Activity

Zero-point-two milliliter of 1M potassium phosphate buffer (pH 7.0), 2.0 mL of 1M D-glucose, 0.2 mL of 25 mM 4-aminoantipyrine, 0.2 mL of 420 mM phenol, 0.2 mL of 1 mg/mL peroxidase and 0.2 mL of ultrapure water were mixed, and then 0.1 mL of the mixed liquid was introduced into a 96-well plate and kept at 25° C. for 5 minutes. Zero-point-one milliliter of the ZeGLD or HsGLD was added, and the reaction was initiated. The variation in absorbance at 500 nm associated with progression of the enzyme reaction was measured for 5 minutes from the initiation of the reaction by using the above-mentioned plate reader to examine the GOD activity. Note that, as a control, water was added instead of GLD so as to initiate the reaction. As a result, no variation in absorbance was observed for ZeGLD and HsGLD as with the control.

From this result, it was confirmed that the GLD of the present invention does not have glucose oxidase activity. Therefore, it was demonstrated that since the GLD of the present invention does not utilize oxygen as an electron acceptor, it is hardly affected by dissolved oxygen in a reaction system in quantifying D-glucose.

(3) Substrate Specificity

D-glucose or maltose of the final concentration of 50 mM were respectively used as a substrate to measure the activity of ZeGLD or HsGLD on each substrate according to the above-mentioned method for measuring GLD activity. Table 1 shows the activity against maltose when the activity against D-glucose is 100.

TABLE 1

|  | ZeGLD | HsGLD |
| --- | --- | --- |
| D-Glucose | 100% | 100% |
| Maltose | 1.2% | 0.9% |

When the activity for D-glucose was taken to be 100%, the GLD of the present invention had activity of 1.2% or 0.9%, i.e., no more than 2.0%, for maltose.

Example 4

(Measurement of Glucose by Means of Absorbance Meter)

The ZeGLD and HsGLD obtained in Example 2 were used to measure variation in absorbance of 0, 1, 2, 5, 10, 20, 50 or 100 mM of D-glucose according to the above-mentioned method for measuring GLD activity. Values of relative activity in each glucose concentration were shown in FIG. 1. As a result, an increase of the activity was observed dependent on the concentration of D-glucose in the D-glucose measurement by using the absorbance meter, which means that D-glucose could be quantified with the GLDs of the present invention.

The invention claimed is:

1. A flavin-conjugated glucose dehydrogenase having the following amino acid sequence (a), (b) or (c), and having glucose dehydrogenase activity:
   (a) the amino acid sequence of SEQ ID NO: 3, 6, 15 or 16;
   (b) an amino acid sequence in which 1 to 3 amino acids are deleted from, replaced in or added to the amino acid sequence of SEQ ID NO: 3, 6, 15 or 16;
   (c) an amino acid sequence which has at least 90% identity with the amino acid sequence of SEQ ID NO: 3 or 15, or an amino acid sequence which has at least 90% identity with the amino acid sequence of SEQ ID NO: 6 or 16.

2. A method for measuring glucose using the flavin-conjugated glucose dehydrogenase according to claim 1.

3. A reagent composition for measuring glucose, containing the flavin-conjugated glucose dehydrogenase according to claim 1.

4. A biosensor for measuring glucose, containing the flavin-conjugated glucose dehydrogenase according to claim 1.

5. The flavin-conjugated glucose dehydrogenase of claim 1, wherein the amino acid sequence of (c) has at least 95% identity with the amino acid sequence of SEQ ID NO: 3 or 15, or at least 95% identity with the amino acid sequence of SEQ ID NO: 6 or 16.

* * * * *